US009877701B2

(12) United States Patent
Kierulf et al.

(10) Patent No.: US 9,877,701 B2
(45) Date of Patent: Jan. 30, 2018

(54) METHODS AND SYSTEMS FOR AUTOMATIC SETTING OF COLOR FLOW STEERING ANGLE

(71) Applicant: General Electric Company, Schenectady, NY (US)

(72) Inventors: Trond Kierulf, Asgardstrand (NO); Trond Kleveland, Holmestrand (NO); Jan Otto Strand, Vear (NO)

(73) Assignee: General Electric Company, Schenectady, NY (US)

( * ) Notice: Subject to any disclaimer, the term of this patent is extended or adjusted under 35 U.S.C. 154(b) by 456 days.

(21) Appl. No.: 14/484,132

(22) Filed: Sep. 11, 2014

(65) Prior Publication Data

US 2016/0074010 A1     Mar. 17, 2016

(51) Int. Cl.
| *A61B 8/14* | (2006.01) |
| *A61B 8/00* | (2006.01) |
| *A61B 8/06* | (2006.01) |
| *A61B 8/08* | (2006.01) |

(52) U.S. Cl.
CPC ............... *A61B 8/469* (2013.01); *A61B 8/06* (2013.01); *A61B 8/5246* (2013.01); *A61B 8/145* (2013.01); *A61B 8/4427* (2013.01); *A61B 8/463* (2013.01); *A61B 8/488* (2013.01); *A61B 8/54* (2013.01)

(58) Field of Classification Search
CPC ......... A61B 8/469; A61B 8/5246; A61B 8/06; A61B 8/54; A61B 8/488; A61B 8/463; A61B 8/145; A61B 8/4427
USPC ................................................. 600/437–469
See application file for complete search history.

(56) References Cited

U.S. PATENT DOCUMENTS

| 2008/0114239 A1* | 5/2008 | Randall ............... G01S 7/52073 600/437 |
| 2008/0114255 A1* | 5/2008 | Schwartz ................. A61B 8/00 600/474 |
| 2010/0240992 A1* | 9/2010 | Hao ......................... A61B 8/00 600/437 |
| 2010/0317971 A1* | 12/2010 | Fan .......................... A61B 8/08 600/439 |
| 2011/0144544 A1* | 6/2011 | Fan .......................... A61N 7/02 601/2 |

* cited by examiner

*Primary Examiner* — Sanjay Cattungal
(74) *Attorney, Agent, or Firm* — McCoy Russell LLP

(57) ABSTRACT

Systems and methods for automatically controlling a color flow steering angle during ultrasonic color flow imaging are provided. In one embodiment, a method for ultrasound imaging comprises automatically adjusting a color flow steering angle responsive to an adjustment of a focal depth setting. In this way, a sensitivity to color flow data may be increased by maintaining a constant overlap between a color flow image and a B-mode image, thereby increasing the accuracy of color flow imaging.

21 Claims, 3 Drawing Sheets

METHODS AND SYSTEMS FOR AUTOMATIC SETTING OF COLOR FLOW STEERING ANGLE

FIELD

Embodiments of the subject matter disclosed herein relate to ultrasound imaging techniques, and more particularly, to color flow imaging techniques.

BACKGROUND

Conventional ultrasound scanners create two-dimensional B-mode images of tissue in which the brightness of a pixel is based on the intensity of the echo return. In a so-called "color flow" mode, the flow of blood or movement of tissue can be imaged. Conventional ultrasound flow imaging techniques use either the Doppler principle or a time-domain cross-correlation method to estimate the average flow velocity, which is then displayed in color overlaid on a B-mode image.

Measurement of blood flow in the heart and vessels using the Doppler effect is well known. The frequency shift of back-scattered ultrasound waves may be used to measure the velocity of the back-scattered waves from tissue or blood. The change or shift in back-scattered frequency increase when blood flows towards the transducer and decreases when blood flows away from the transducer. The Doppler shift may be processed to estimate the average flow velocity, which is displayed using different colors to represent speed and direction of flow. The color flow velocity mode displays hundreds of adjacent sample volumes simultaneously, all color-coded to represent each sample volume's velocity. Hence such Doppler shifts measured in a color flow imaging mode may be referred to hereinafter as color flow data.

The sensitivity of an ultrasound imaging system to color flow data, or the ability of the ultrasound imaging system to detect Doppler shifts from ultrasonic waves reflected from flowing blood, depends on a color flow steering angle, where the color flow steering angle comprises an angle between a color flow region of interest and a B-mode image. For example, a color flow steering angle of zero corresponds to a color flow region of interest completely overlapping the underlying B-mode image, and results in low color flow sensitivity. As the color flow steering angle increases, the color flow sensitivity increases. However, if the color flow steering angle is too large, the color flow region of interest will not overlap the B-mode image at all and the color flow sensitivity is moot.

Furthermore, a user of an ultrasound imaging system may adjust the focal depth of the ultrasound image in order to view particular structures within a patient. For shallow focal depths, a large color flow steering angle will result in high color flow sensitivity. As the focal depth is increased, however, the color flow steering angle must be decreased to ensure that the color flow region of interest overlaps the underlying B-mode image.

Thus, for conventional ultrasound imaging systems, a user needs to perform multiple operations—adjusting a focal depth and subsequently adjusting a color flow steering angle—to obtain optimized images, which is time consuming and user dependent. Furthermore, an inexperienced user may generate suboptimal images, thereby increasing risk of an incorrect diagnosis. Further still, some ultrasound imaging systems may be portable, handheld devices and therefore may include a limited number of user control inputs. As a result, the process of calibrating a color flow imaging mode may be more complex, further increasing the difficulty of obtaining optimized ultrasound images and increasing the risk of an incorrect diagnosis. The inventors have recognized the above issues and have devised several approaches to address them.

BRIEF DESCRIPTION

In one embodiment, a method for ultrasound imaging comprises automatically adjusting a color flow steering angle responsive to an adjustment of a focal depth setting. In this way, a sensitivity to color flow data may be increased by maintaining a constant overlap between a color flow image and a B-mode image, thereby increasing the accuracy of color flow imaging in an ultrasound imaging system with a reduced number of user inputs.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE FIGURES

The present invention will be better understood from reading the following description of non-limiting embodiments, with reference to the attached drawings, wherein below.

DETAILED DESCRIPTION

Figure 2:
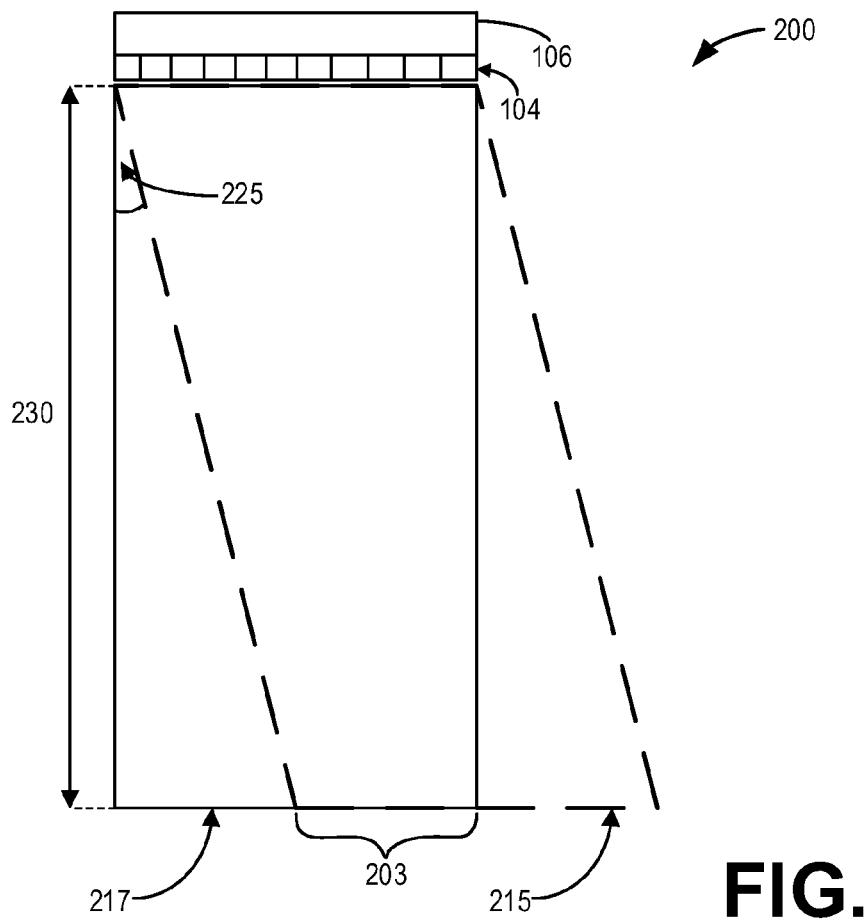
FIG. 2 shows a diagram illustrating a color flow region of interest overlaid a B-mode image at a long depth.
Figure 3:
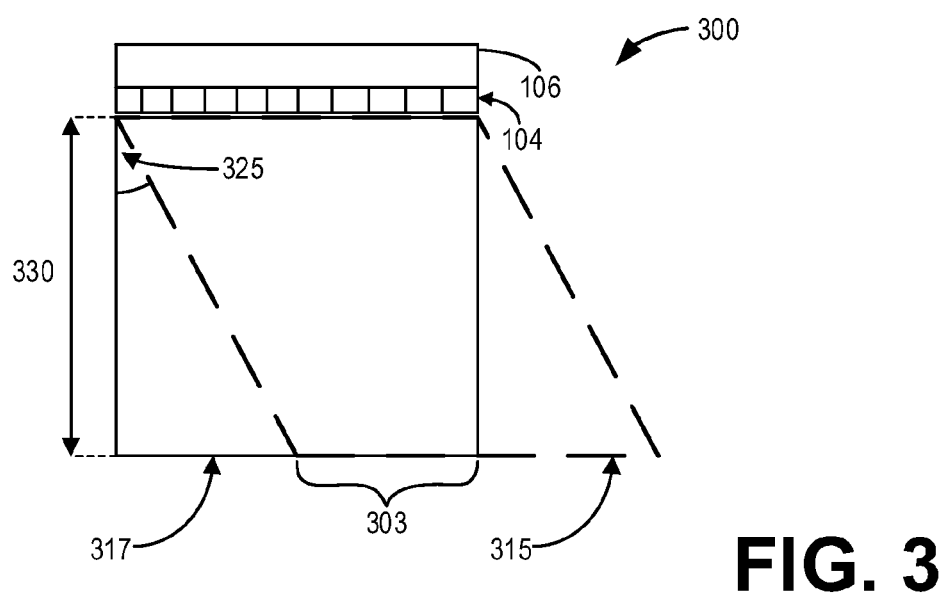
FIG. 3 shows a diagram illustrating a color flow region of interest overlaid on a B-mode image at a short depth.

The following description relates to various embodiments of ultrasound imaging techniques. In particular, methods and systems for automatically controlling a color flow steering angle during ultrasonic color flow imaging are provided. An ultrasound imaging system such as the system shown in FIG. 1 may include a color flow imaging mode wherein color images of the velocity of moving material, such as blood, are superimposed over a grayscale anatomical B-mode image. In order to maintain a constant overlap between a color flow region of interest, wherein the color images are formed, and the underlying B-mode image when adjusting the ultrasound focal depth, a color flow steering angle may be adjusted based on the focal depth as illustrated in FIGS. 2 and 3. The color flow steering angle may be automatically adjusted when focal depth adjustments are made using the method shown in FIG. 4.

Figure 1:
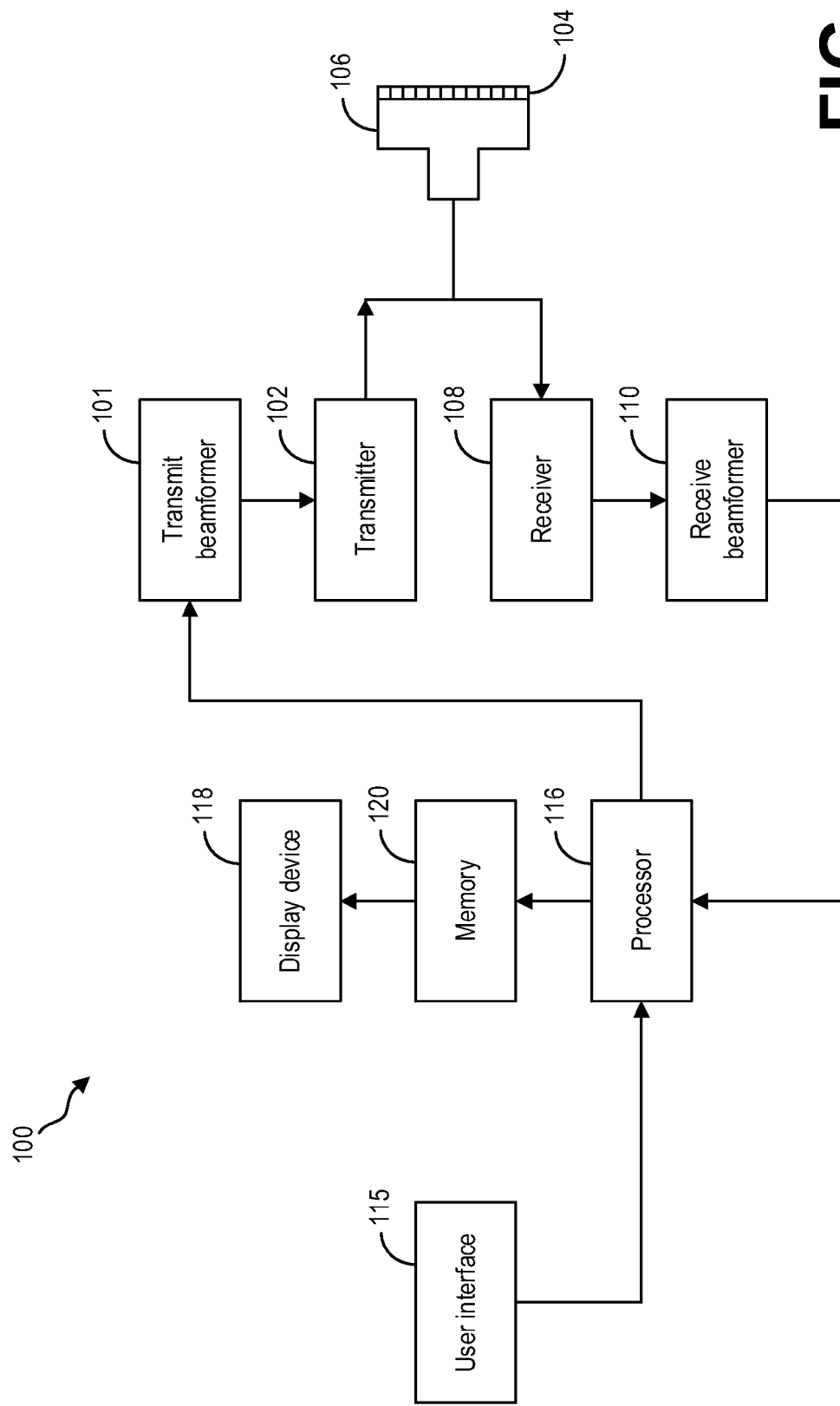
FIG. 1 shows an ultrasonic imaging system according to an embodiment of the invention.

FIG. 1 is a schematic diagram of an ultrasound imaging system 100 in accordance with an embodiment of the invention. The ultrasound imaging system 100 includes a transmit beamformer 101 and a transmitter 102 that drive elements 104 within a transducer array, or probe, 106 to emit pulsed ultrasonic signals into a body (not shown). According to an embodiment, the transducer array 106 may be a one-dimensional transducer array probe. However, in some embodiments, the transducer array 106 may be a two-dimensional matrix transducer array probe. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including to control the input of patient data, to change a scanning or display parameter, and the like. The user interface 115 may include one or more of the following: a rotary, a mouse, a keyboard, a trackball, hard keys linked to specific actions, soft keys that may be configured to control different functions, and a graphical user interface displayed on the display device 118.

The ultrasound imaging system 100 also includes a processor 116 to control the transmit beamformer 101, the transmitter 102, the receiver 108, and the receive beamformer 110. The processor 116 is in electronic communication with the probe 106. For purposes of this disclosure, the term "electronic communication" may be defined to include both wired and wireless communications. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. A memory 120 is included for storing processed volumes of acquired data. In an exemplary embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. The image lines and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed.

In various embodiments of the present invention, one or more components of ultrasound imaging system 100 may be included in a portable, handheld ultrasound imaging device. For example, display device 118 and user interface 115 may be integrated into the exterior surface of the handheld ultrasound imaging device, which may further contain processor 116 and memory 120. Transducer array 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

In embodiments where ultrasound imaging system 100 comprises a portable, handheld ultrasound imaging device, user interface 115 may include limited user input controls due to considerations of a size of the device. For example, user interface 115 may include a small subset of the control inputs generally available in the user interface of a standard ultrasound imaging system. As a result, a user may encounter greater difficulty achieving optimal sensitivity when using, for example, a color Doppler imaging mode.

For example, in traditional ultrasound imaging systems, user interface 115 may include an input control that allows a user to control a color flow steering angle, or the angle between a color flow region of interest and an underlying B-mode image. Color flow imaging occurs within the region where the color flow region of interest and the underlying B-mode image overlap. The color flow steering angle affects color flow sensitivity, or the system's ability to image color flow signals. For a color flow steering angle of zero, the color flow region of interest is directed normal to the transducer array and the color flow sensitivity is very low. As the color flow steering angle is increased, the color flow sensitivity increases. In particular, color flow sensitivity increases as the color flow steering angle, or beam direction, becomes more parallel to the angle of the flow velocity, or the direction of blood flow. In typical clinical applications, the B-mode ultrasound beam images blood vessels at a 90 degree (normal) angle to the direction of blood flow, and thus the color flow sensitivity increases as the color flow steering angle increases (otherwise, because the vessel is close to normal to the beam direction, low sensitivity may be experienced). However, as the color flow steering angle increases, the overlap between the color flow region of interest and the B-mode image decreases, thereby narrowing the field of view of the region of interest.

As a user adjusts a focal depth of the ultrasound beam so that structures of interest may be imaged, the user must also adjust the color flow steering angle to ensure that the color flow region of interest overlaps the underlying B-mode image. For example, the color flow steering angle may be reduced as the focal depth is increased to ensure the color flow region of interest and the underlying B-mode image overlap, and similarly the color flow steering angle may be increased as the focal depth is decreased. However, in embodiments where ultrasound imaging system 100 comprises a handheld ultrasound imaging device, user interface 115 may include one or more buttons for increasing and decreasing the focal depth but may not include a control input to adjust a color flow steering angle. As described further herein with regard to FIG. 4, when a user adjusts the focal depth of the ultrasound beam, processor 116 may automatically compute a color flow steering angle based on the focal depth and accordingly adjust the color flow steering angle in order to maintain a constant overlap between the color flow region of interest and the underlying B-mode image. In this way, color flow sensitivity may be increased for an ultrasound imaging system 100 with a reduced number of user inputs. The relationship between a color flow steering angle, the focal depth, the B-mode image, and the color flow region of interest are described further herein with regard to FIGS. 2 and 3.

FIG. 2 shows a diagram 200 illustrating an overlap 203 of a color flow region of interest 215 and a B-mode image 217. In particular, diagram 200 depicts the relationship between a color flow steering angle 225 and a focal depth 230.

As described hereinabove, a transducer array 106 containing a plurality of transducer elements 104 may emit a plurality of ultrasonic waves into a subject (not shown) and receive the back-scattered waves, which may in turn be used to form ultrasound images. For example, back-scattered ultrasound waves may be used to form an ultrasound B-mode (static, grayscale) image 217 of anatomical structure at a focal depth 230. The plurality of ultrasound waves may be steered at a color flow steering angle 225 towards a color flow region of interest 215, and the back-scattered ultrasound waves may be used to form dynamic, color-coded images depicting blood flow velocities in an overlapping region 203. The combined B-mode image and the superimposed color flow image are displayed on display device 118. However, the portion of the color flow region of interest 215 that does not overlap with the B-mode image 217 is not displayed on display device 118, and is therefore irrelevant.

If the color flow steering angle 225 equals zero, the color flow region of interest 215 completely overlaps the B-mode image 217. However, in this case the color flow sensitivity is very low, resulting in a color flow ultrasound image of very low quality. Thus a non-zero color flow steering angle 225 is desired.

In some embodiments, a constant overlap 203 may be specified such that the percentage of a B-mode image 217 that is covered by a color flow region of interest 215 is constant, regardless of the focal depth. As illustrated by FIG. 3, the color flow steering angle 225 may be adjusted in order to maintain the constant overlap 203 for a different focal depth.

FIG. 3 shows a diagram 300 illustrating an overlap 303 of a color flow region of interest 315 and a B-mode image 317. In particular, diagram 300 depicts the formation of a color flow ultrasound image at a shallow focal depth 330. In order to maintain the same overlap 303 as the overlap 203 depicted in FIG. 2 for a smaller focal depth 330, the color flow steering angle 325 must be increased in comparison to color flow steering angle 225 as shown.

For conventional ultrasound imaging systems, a user manually adjusts the focal depth and then manually adjusts the color flow steering angle in order to establish a desired overlap between a color flow region of interest and a B-mode image. However, as discussed hereinabove with regard to FIG. 1, such manual adjustments may be impractical for ultrasound imaging systems with limited user inputs. Furthermore, for any ultrasound imaging system, such manual control may be time consuming and user dependent. As described further herein with regard to FIG. 4, the color flow steering angle may be automatically adjusted such that a constant overlap is maintained while a user adjusts a focal depth. In this way, the process of color flow imaging may become more time efficient and less prone to user error.

Figure 4:
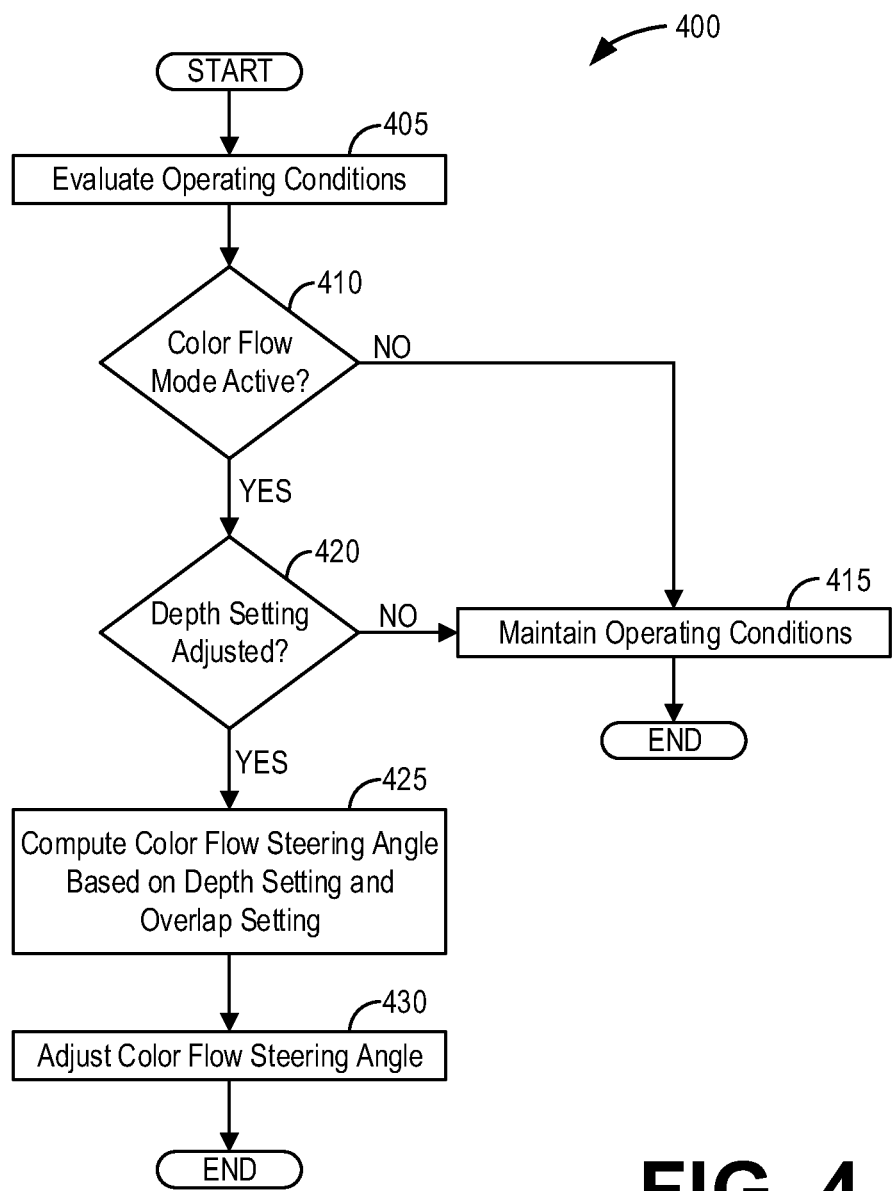
FIG. 4 shows a high-level flow chart illustrating an example method for automatically adjusting a color flow steering angle responsive to a depth adjustment.

FIG. 4 shows a high-level flow chart illustrating an example method 400 for maintaining a constant overlap between a color flow box and an underlying B-mode image. In particular, method 400 relates to the automatic adjustment of a color flow steering angle in response to the adjustment of an ultrasound beam focal depth. Method 400 will be described herein with reference to the system depicted in FIGS. 1-3, though it should be understood that the method may be applied to other systems without departing from the scope of this disclosure. Method 400 may be carried out by processor 116, and may be stored as executable instructions in non-transitory memory of the processor 116.

Method 400 begins at 405. At 405, the method 400 may include evaluating operating conditions of the ultrasound imaging system 100. Operating conditions may include, but are not limited to, a focal depth, an active imaging mode, an overlap setting defining a desired overlap of a color flow region of interest with an underlying B-mode image, and so on. The overlap setting may comprise a percentage of the B-mode image that the color flow region of interest should overlap. For example, the overlap setting may be 50%, and so the color flow region of interest may overlap half of the B-mode image. In other examples, the overlap setting may be greater than or less than 50%. Furthermore, the overlap setting may be a static value, or may be based on the focal depth. In another example, color flow sensitivity at a given color flow steering angle and focal depth may be dependent on the blood flow velocities being imaged. For example, echo signals from very low velocity blood flow may be difficult to separate from surrounding tissue. As such, the overlap setting may be automatically adjusted to an optimal setting based on imaged blood flow velocities. After evaluating operating conditions of the ultrasound imaging system, method 400 proceeds to 410.

At 410, method 400 may include determining if a color flow imaging mode is the active imaging mode. If the color flow imaging mode is not active, method 400 proceeds to 415, where the operating conditions of the ultrasound imaging system 100 evaluated at 405 are maintained. Method 400 may then end. Returning to 410, if the color flow imaging mode is active, method 400 proceeds to 420.

At 420, method 400 may include determining if a focal depth setting is adjusted. If the focal depth setting is not adjusted, method 400 proceeds to 415, where the operating conditions evaluated at 405 are maintained. Method 400 may then end. Returning to 420, if the focal depth setting is adjusted, method 400 proceeds to 425.

At 425, method 400 may include computing a color flow steering angle based on the adjusted focal depth setting and the overlap setting. As shown in FIGS. 2 and 3, the focal depth setting defines the distance from the transducer to the anatomical structure in the B-mode image, while the overlap setting defines the distance of the overlap region in the B-mode image. Thus computing the color flow steering angle is a matter of solving a trigonometric equation, such as the Pythagorean equation, using the focal depth setting and the overlap setting, where the overlap setting may be used to determine the distance of the B-mode image that does not overlap with the color flow region of interest.

At 430, method 400 may include adjusting the color flow steering angle to the color flow steering angle computed at 420. Adjusting the color flow steering angle may comprise adjusting time delays of ultrasound waves emitted from transducer elements 104 in order to steer the ultrasound waves towards the color flow region of interest. In accordance with the present invention, such adjustment may automatically occur without further user input. Method 400 may then end.

In some examples, the overlap setting may be specified by a user input. In other examples, the overlap setting may be determined at the time of manufacturing ultrasound imaging system 100. In yet other examples, the overlap setting may be automatically determined from the focal depth setting such that color flow sensitivity is optimized for all focal depths.

In some embodiments, the color flow region of interest may be smaller than the B-mode image in multiple dimensions, and therefore the color flow steering angle may comprise one or more steering angles. In such embodiments, computing a color flow steering angle may comprise computing one or more color flow steering angles as described hereinabove.

The approach described herein eliminates the need for a user to manually adjust the position of a color flow region of interest when imaging a structure of interest. The technical effect of the disclosure may include the automatic adjustment of one or more color flow steering angles to maintain a constant overlap between a color flow region of interest and a B-mode image. In this way, an increased sensitivity of color flow imaging may be achieved with minimal user input. As a result, another technical effect of the disclosure may include the creation of high quality color flow images. In this way, the likelihood of an incorrect diagnosis due to suboptimal medical images may be decreased.

In one embodiment, a method for ultrasound imaging comprises automatically adjusting a color flow steering angle responsive to an adjustment of a focal depth. In one example, adjusting the color flow steering angle is based on the focal depth and an overlap. For example, the overlap may comprise a percentage of a color flow region of interest that overlaps a B-mode image. Adjusting the color flow steering angle comprises adjusting time delays of ultrasonic waves emitted from a plurality of transducer elements. In one example, the adjustment of the focal depth is received from a user input in a handheld ultrasound imaging device. In another example, the handheld ultrasound imaging device does not include a user input for manually adjusting the color flow steering angle.

In another embodiment, a method for ultrasound imaging comprises receiving a focal depth from a user input, adjusting a frequency of ultrasound waves emitted from a plurality of transducer elements based on the focal depth, generating a B-mode image from a first set of ultrasound echoes from the ultrasound waves emitted at the adjusted frequency, computing a color flow steering angle based on the focal depth and a specified overlap, adjusting time delays of the ultrasonic waves emitted from the plurality of transducer elements based on the color flow steering angle, generating a color flow image from a second set of ultrasound echoes from the ultrasound waves emitted with the time delays at the adjusted frequency, and displaying the color flow image superimposed over the B-mode image.

In one example, the specified overlap is automatically specified and based on the focal depth. In another example, the specified overlap is specified by a user. In yet another example, the specified overlap is specified at a time of manufacturing and invariant thereafter.

In one example, the user input comprises at least one button on a handheld ultrasound imaging device. In another example, the handheld ultrasound imaging device includes a display screen, and displaying the color flow image superimposed over the B-mode image comprises displaying the color flow image superimposed over the B-mode image on the display screen. In some examples, the user input does not include a control for manually adjusting the color flow steering angle. In other examples, a user cannot manually adjust the color flow steering angle when adjusting the focal depth.

In yet another embodiment, an ultrasound imaging system comprises: a transducer array including a plurality of array elements, the transducer array adapted to transmit and receive a plurality of ultrasound waves; a display configured to display a color flow image superimposed over a B-mode image; a user interface including at least one button, the at least one button configured to adjust a focal depth; and a processor configured with computer readable instructions for automatically adjusting a color flow steering angle responsive to an adjusted focal depth. In one example, the ultrasound imaging system is housed in a handheld enclosure. In another example, the user interface further includes at least one user input for adjusting the color flow steering angle.

In some examples, a user cannot manually adjust the color flow steering angle when manually adjusting the focal depth. In other examples, a user cannot manually adjust the focal depth when manually adjusting the color flow steering angle. In one example, the color flow steering angle is automatically adjusted to maintain a constant overlap between the color flow image and the B-mode image.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for ultrasound imaging, comprising:
generating a B-mode image from a first set of ultrasound data;
determining a color flow steering angle;
receiving a user input for an adjustment to a focal depth;
automatically adjusting the color flow steering angle responsive to the adjustment of the focal depth; and
displaying a color flow image superimposed over the B-mode image, the color flow image generated from a second set of ultrasound data acquired with the adjusted color flow steering angle.

2. The method of claim 1, wherein adjusting the color flow steering angle is based on the focal depth and an overlap, the overlap comprising a percentage of a color flow region of interest that overlaps the B-mode image.

3. The method of claim 2, wherein the overlap is held constant as the focal depth and the color flow steering angle are adjusted.

4. The method of claim 1, wherein adjusting the color flow steering angle comprises adjusting time delays of ultrasonic waves emitted from a plurality of transducer elements.

5. The method of claim 1, wherein the adjustment of the focal depth is received from the user input in a handheld ultrasound imaging device.

6. The method of claim 5, wherein the handheld ultrasound imaging device does not include a user input for manually adjusting the color flow steering angle.

7. A method for ultrasound imaging, comprising:
receiving a focal depth from a user input;
adjusting a frequency of ultrasound waves emitted from a plurality of transducer elements based on the focal depth;
generating a B-mode image from a first set of ultrasound echoes from the ultrasound waves emitted at the adjusted frequency;
computing a color flow steering angle based on the focal depth and a specified overlap;
adjusting time delays of the ultrasound waves emitted from the plurality of transducer elements based on the color flow steering angle;
generating a color flow image from a second set of ultrasound echoes from the ultrasound waves emitted with the time delays at the adjusted frequency; and
displaying the color flow image superimposed over the B-mode image.

8. The method of claim 7, wherein the specified overlap is automatically specified and based on the focal depth.

9. The method of claim 7, wherein the specified overlap is specified by a user.

10. The method of claim 7, wherein the specified overlap is specified at a time of manufacturing and invariant thereafter.

11. The method of claim 7, wherein the user input comprises at least one button on a handheld ultrasound imaging device.

12. The method of claim 11, wherein the handheld ultrasound imaging device includes a display screen, and displaying the color flow image superimposed over the B-mode image comprises displaying the color flow image superimposed over the B-mode image on the display screen.

13. The method of claim 11, wherein the user input does not include a control for manually adjusting the color flow steering angle.

14. The method of claim 7, wherein a user cannot manually adjust the color flow steering angle when adjusting the focal depth.

15. An ultrasound imaging system, comprising:
a transducer array including a plurality of array elements, the transducer array adapted to transmit and receive a plurality of ultrasound waves;
a display configured to display a color flow image superimposed over a B-mode image;

a user interface including at least one user input control, the at least one user input control configured to adjust a focal depth; and a processor configured with computer readable instructions for automatically adjusting a color flow steering angle responsive to the adjusted focal depth.

16. The system of claim 15, wherein the ultrasound imaging system is housed in a handheld enclosure.

17. The system of claim 15, wherein the user interface further includes at least one user input for adjusting the color flow steering angle.

18. The system of claim 17, wherein a user cannot manually adjust the color flow steering angle when manually adjusting the focal depth.

19. The system of claim 17, wherein a user cannot manually adjust the focal depth when manually adjusting the color flow steering angle.

20. The system of claim 15, wherein the color flow steering angle is automatically adjusted to maintain a constant overlap between the color flow image and the B-mode image.

21. The system of claim 15, wherein the at least one user input control comprises a button.

* * * * *